US006177451B1

(12) United States Patent
Qian et al.

(10) Patent No.: US 6,177,451 B1
(45) Date of Patent: Jan. 23, 2001

(54) EPIBATIDINE AND DERIVATIVES THEREOF AS NICOTINE CHOLINERGIC RECEPTOR AGONISTS

(75) Inventors: Changgeng Qian, Wayland; Tongchuan Li, Framingham; Tesfaye Biftu, Belmont, all of MA (US); Tsung-Ying Shen, Charlottesville, VA (US)

(73) Assignee: UCB, S.A., Brussels (BE)

( * ) Notice: Under 35 U.S.C. 154(b), the term of this patent shall be extended for 0 days.

(21) Appl. No.: 08/476,611

(22) Filed: Jun. 7, 1995

Related U.S. Application Data

(62) Division of application No. 08/119,697, filed on Sep. 10, 1993, now abandoned.

(51) Int. Cl.[7] ................................................... A61K 31/44
(52) U.S. Cl. ........................ 514/343; 514/304; 514/339; 514/413; 514/397; 514/253; 514/256
(58) Field of Search .................................. 514/304, 339, 514/413, 397, 253, 256, 343

(56) References Cited

U.S. PATENT DOCUMENTS

| | | | |
|---|---|---|---|
| 4,835,162 | 5/1989 | Abood | 514/305 |
| 4,910,193 * | 3/1990 | Buchheit | 514/299 |
| 4,940,703 | 7/1990 | Baker et al. | 514/210 |
| 4,966,916 | 10/1990 | Abood | 514/534 |
| 4,992,436 | 2/1991 | Baker et al. | 514/215 |
| 5,104,989 | 4/1992 | Cottrell et al. | 546/112 |
| 5,106,853 | 4/1992 | Showell et al. | 514/299 |
| 5,124,460 * | 6/1992 | Humphrey | 548/731 |
| 5,128,118 * | 7/1992 | Carroll et al. | 514/304 |
| 5,219,860 | 6/1993 | Chambers et al. | 514/278 |
| 5,227,385 * | 7/1993 | Caldwell et al. | 514/304 |
| 5,242,927 | 9/1993 | Baker et al. | 514/299 |
| 5,242,930 | 9/1993 | Baker et al. | 514/305 |
| 5,256,671 | 10/1993 | Ladduwahetty et al. | 514/305 |
| 5,260,293 | 11/1993 | Baker et al. | 514/214 |
| 5,288,730 | 2/1994 | Baker et al. | 514/305 |
| 5,314,899 | 5/1994 | Daly et al. | 514/339 |
| 5,324,723 | 6/1994 | Baker et al. | 514/212 |
| 5,405,853 | 4/1995 | Baker et al. | 514/299 |
| 5,426,106 | 6/1995 | Kulagowski et al. | 514/233 |
| 5,432,177 | 7/1995 | Baker et al. | 514/253 |
| 5,444,074 | 8/1995 | Baker et al. | 514/326 |
| 5,451,588 | 9/1995 | Baker et al. | 514/323 |
| 5,459,270 | 10/1995 | Williams et al. | 546/152 |
| 5,461,063 | 10/1995 | Kelleher et al. | 514/312 |

FOREIGN PATENT DOCUMENTS

| | | | |
|---|---|---|---|
| 6312989 | 11/1994 | (JP) | C07D/487/08 |
| 7010878 | 1/1995 | (JP) | C07D/487/08 |
| WO 93/18037 | 9/1993 | (WO) | C07D/487/08 |
| WO 94/04152 | 3/1994 | (WO) | A61K/31/465 |
| WO 94/07489 | 4/1994 | (WO) | A61K/31/41 |
| WO 94/22868 | 10/1994 | (WO) | C07D/487/08 |

OTHER PUBLICATIONS

Abstracts of Poster Presentations Nos. 1–97, "The Otto Loewi New Investigator Awards for 1995," *Life Sciences*, 56(11/12):1001–1050 (1995).

Adamus, et al., "Phase I Clinical Trials with WAL2014, A New Muscarinic Agonist for the Treatment of Alzheimer's Disease," *Life Sciences*, 56:(11/12):883–890 (1995) (Elsevier Sciences, Ltd., Editors).

Ainsworth, et al., "Alkyl–1,3,4–oxadiazoles," *J. Org. Chem.*, 31:3442–3444 (1966).

Altenbach, H.J., et al., "7–Azanorbornadiene," *Angew Chem. Int. Ed. Engl.*, 21(10):778 (1992).

Altenbach, H.J., et al., "Syntheses and Photoelectron Spectra of 7–Azanorbornadiene and Related Compounds. An Analysis with Fragment Orbitals," *Chem. Ber.* 124:791–801 (1991).

Badio and Daly, "Epibatidine, a Potent Analgetic and Nicotinic Agonist," *Mol. Pharmacol.*, 45:563–569 (1994).

Badio and Daly, "Epibatidine. A potent analgetic and nicotinic agonist," *FASEB Journal*, 8(4–5):A875 (1994).

Baker and Saunders, "Central Muscarinic Ligands and Receptors," *Ann. Rep. in Med. Chem.* Chapter 4, 24:31–39 (1989).

Bansal, et al., "Influence of Lewis acids on the Diels–Alder reaction. Part I. An improved synthesis of 7–azanorbornadiene, 3–azaquadricyclaine, and azepine derivatives," *Can. J. Chem.*, 47:2391–2394 (1969).

Barber, and Gottschlich, "Opioid Agonists and Antagonists: An Evaluation of Their Peripheral Actions in Inflammation," *Medicinal Research Review*, 12(5):525–562 (1992).

Barnes, et al., "Tiotropium Bromide (Ba 679 BR), a Novel, Long–Acting Muscarinic Antagonist for the Treatment of Obstructive Airways Disease," *Life Sciences*, 56:(11/12):853–859 (1995) (Elsevier Science, Ltd., Editors).

(List continued on next page.)

Primary Examiner—Keith D. MacMillan
(74) Attorney, Agent, or Firm—McDonnell Boehnen Hulbert & Berghoff

(57) ABSTRACT

The present invention provides methods of treatment utilizing pharmaceutical compositions comprising an effective nicotine agonist amount of epibatidine (1) or a synthetic 7-azabicyclo[2.2.1]-heptane or heptene derivative thereof, and a pharmaceutically acceptable carrier, excipient or diluent.

(1)

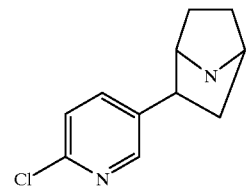

1 Claim, No Drawings

OTHER PUBLICATIONS

Bhattacharya, S.N., et al., "Friedel–Crafts Sulphonylation of Bis(trimethylsily)acetylene: a Useful Route to Aryl Ethynyl Sulphones," *Organomet. Chem. Synth.,* 1:145–149 (1970).

Bittoun, "Recurrent aphthous ulcers and nicotine," *Med. J. Australia,* 154:471–472 (1991).

Bradley, "Frog Venom Cocktail Yields A One–Handed Painkiller," *Science* 261:1117 (1993).

Broka, C.A., "Total Synthesis of Epibatidine," *Tet. Lett.,* 34(20):3251–3254 (1993).

Burgen, "The Background of the Muscarinic System," *Life Sciences,* 56(11/12):801–806 (1995) (Elsevier Science, Ltd., Editors).

Burke, et al., "Construction of a Molecular Shape Analysis–Three–Dimensional Quantitative Structure–Analysis Relationship for an Analog Series of Pyridobenzodiazepinone Inhibitors of Muscarinic 2 and 3 Receptors," *J. Med. Chem.,* 37:3775–3788 (1994).

Chen, et al., "Synthesis of the Epibatidine Ring System from Pyrroles via Their Pentaammineosmium(II) Complexes," *Am. Chem. Soc. Meeting,* Denver, Colorado (Mar. 28–Apr. 2, 1993).

Christensen, et al., "Antinociceptive effects of the stereoisomers of nicotine given intrathecally in spinal rats," *J. Neural. Transm. GenSec.,* 80:189–194 (1990).

Clayton and Regan, "A Total Synthesis of (+/-) Epibatidine," *Tetrahedron Letters,* 34(46):7493–7496 (1993).

Cooley, et al., "Effect of pCPA on Nicotine–Induced Analgesia," *Pharmacol. Biochem. Behav.,* 36:413–415 (1990).

Cordone, R., et al., "π–Heterocyclic Complexes of Pentaammineosmium(II) and the Metal–Induced Cycloaddition of Pyrrole and Maleic Anhydride," *J. Am. Chem. Soc.,* 111:5969–5970 (1989).

Corey, E.J., et al., "Stereocontrolled Total Synthesis of (+)– and (−)– epibatidine," *J. Org. Chem.,* 58:(21):5600–5602 (1983).

Daly, et al., "A New Class of Indolizidine Alkaloids from the Poison Frog, Dendrobates tricolor. X–ray Analysis of 8–Hydroxy–8–methyl–6–(2'–methylhexylidene)–1–azabicyclo[4.3.0]nonane," *J. Am. Chem. Soc.,* 102:830–836 (1980).

Davis and Whitham, "Ethylnyl p–Tolyl Sulphone as an Acetylene Equivalent in Diels–Alder Reactions," *J.C.S. Chem. Comm.,* pp. 639 (1980).

Devor and Isenberg, "Nicotine and Tourette's Syndrome," *Lancet,* 2:1046 (1989).

Donnini and Just, "Diels–Alder Reactions of Pyrroles as an Entry to Substituted 3–Oxatropanes and Tetrasubstituted Pyrrolidines," *Heterocycl. Chem.,* 14:1423–1425 (1977).

Drew, et al., "High–pressure Synthesis, Structures, and Conformational Properties of Some Derivatives of 7–Azabicyclo[2.2.1]heptane. X–Ray Determination of endo–10–Benzoyl–4–phenyl–4,10–diazatricyclo[5.2.1.0$^{2,6}$] dec–8–ene–3,5–dione and exo–10–Acetl–4–phenyl–4, 10–diazatricyclo[5.2.1.0$^{2,6}$]decane–3,5–dione," *J.C.S. Perkins Trans I:*1277–1284 (1985).

Dukat, M.; et al., "Epibatidine: A very high affinity nicotine–receptor ligand," *Medicinal Chem. Res.,* 4:131–139 (1994).

Duvoisin, "Cholinergic–Anticholinergic Antagonism in Parkinsonism," *Arch. Neurol.* 17:124–136 (1967).

Ehlert and Thomas, "Functional Role of $M_2$ Muscarinic Receptors in the Guinea Pig Ileum," *Life Sciences,* 56(11/12):965–971 (1995) (Elsevier Science, Ltd., Editors).

Ehringer and Hornykiewicz, "Verteilung Von Noradrenalin Und Dopamin (3–Hydroxytyramin) Im Gehirn Des Menschen Und Ihr Verhalten Bei Erkrankungen Des Extrapyramidalen Systems," *Klin. Wochenschr.,* 38:1236–1239 (1960).

Feriani, et al., "Cholinergic Agents Structurally Related to Furtrethonium. 2. Synthesis and Antimuscarinic Activity of a Series of N–[5–](1'–Substituted–acetoxy)methyl]–2–furfuryl]dialkylamines," *J. Med. Chem.,* 37:4278–4287 (1994).

Fisher, et al., "Epibatidine, An Alkaloid From the Poison Frog Epipedobates tricolor, Is a Powerful Ganglionic Depolarizing Agent," *J. of Pharm. and Exp. Therap.* 270:702–707 (1994).

Fletcher, et al., "The Synthesis of (+) and (−) Epibatidine," *J. Chem. Soc. Chem. Comm.,* 1216–1218 (1993).

Fletcher, S., et al., "Total synthesis and determination of the absolute configuration of epibatidine," *J. Org. Chem.,* 59(7):1771–1778 (1994).

Flynn, et al., "Differential Alterations in Muscarinic Receptor Subtypes in Alzheimer's Disease: Implications for Cholinergic–Based Therapies," *Life Sciences,* 56(11/12):868–876 (1995) (Elsivier Science, Ltd., Editors).

Fraser and Lee, "Regulation of Muscarinic Receptor Expression by Changes in mRNA Stability," *Life Science,* 56(11/12):899–906 (1995) (Elsevier Sciences, Ltd., Editors).

Fraser, et al., "Synthesis of 7–azabicyclo[2.2.1]heptane, exo–2–chloro–7–azabicyclo[2.2.1]heptane, and derivatives," *Can. J. Chem.,* 48:2065–2074 (1970).

Gabel, N.W., "Diels–Alder Reactions of 1–Carbomethoxy––pyrroles and Dimethyl Acetylenedicarboxylate," *J. Org. Chem.,* 27:301–303 (1962).

Garvey, et al., "Novel Isoxazoles which Interact with Brain Cholinergic Channel Receptors Have Intrinsic Cognitive Enhancing and Anxiolytic Activities," *J. Med. Chem.,* 37:1055–1059 (1994).

Garvey, et al., "Synthesis and in Vitro Characterization of Novel Amino Terminally Modified Oxotremorine Derivatives for Brain Muscarinic Receptors," *J. Med. Chem.,* 35:1550–1557 (1992).

Glassman and Covey, "Future Trends in the Pharmacological Treatment of Smoking Cessation" *Drugs,* 40(1): 1–5 (1990).

Goldstein and Shen, "Dual Inhibitors of Platelet Activating Factor and 5–Lipoxygenase II. Novel 2,4–Diaryl–1,3–dithiolanes with Iron–Chelating Functionalities," *Med. Chem. Res.,* 2:451–456 (1992).

Goldstein and Shen, "Dual Inhibitors of Platelet Activating Factor and 5–Lipoxygenase I. 2,4–Diaryl–1,3–dithiolanes," *Med. Chem. Res.,* 2:443–450 (1992).

Gonzalez, J., et al., "Dearomatization of Analines via Complexation to Pentaammineosmium(II): A Novel [2+2+2] Michael–Ring–Closure Reaction of an $n^2$–Coordinated Analine," *Am. Chem. Soc. Mtg.,* 205th ACS National Meeting, Denver CO, Mar. 1993.

Gopalakrishnan and Sullivan, "Targeting Nicotinic Cholinergic Receptors," *Drug News & Perspectives,* 7(7):444–448 (1994).

Gourlay and McNeil, "Antismoking products," *Med. J. Australia,* 153:699–707 (1990).

Grunberg, et al., "Effects of nicotine on body weight and food consumption in rats," *Psychopharmacology,* 83:93–98 (1984).

Hacksell, et al., "Quinuclidin–2–ENE–Based Muscarinic Antagonists," *Life Sciences,* 56(11/12):831–836 (1995) (Elsevier Science, Ltd., Editors).

Hamilton, et al., "Molecular Analysis of the Regulation of Muscarinic Receptor Expression and Function," *Life Sciences,* 56:11/12):939–943 (1995) (Elsevier Science, Ltd., Editors).

Hersch and Levey, "Diverse Pre– and Post–Synaptic Expression of m1–m4 Muscarinic Receptor Proteins in Neurons and Afferents in the Rat Neostriatum," *Life Sciences,* 56(11/12):931–938 (1995) (Elsevier Science, Ltd., Editors).

Hille, et al., "Multiple G–Protein–Coupled Pathways Inhibit N–Type Ca Channels of Neurons," *Life Sciences,* 56(11/12):989–992 (1995) (Elsevier Science, Ltd., Editors).

Hirschberg, et al., "Kinetic and Biophysical Analysis of the m2 Muscarinic Receptor," *Life Sciences,* 56(11/12):907–913 (1995) (Elsevier Science, Ltd., Editors).

Hodges, L.M., et al., "$\eta^2$–Pyrrole Complexes as Synthons to Alkaloid Derivatives," *J. Org. Chem.,* 58:4788–4790 (1993).

Hosey, et al., "Multiple Mechanisms Involving Protein Phosphorylation are Linked to Desensitization of Muscarinic Receptors," *Life Sciences,* 56(11/12):951–955 (1995) (Elsevier Science, Ltd., Editors).

Huang and Shen, "A Versatile Total Synthesis of Epibatidine and Analogs," *Tet. Let.,* 34:4477–4480 (1993).

Huang, D.F., et al., "A Versatile Total Synthesis of Epibatidine and Analogs," *Tetrahedron Letters,* 58:28 4477–4480 (1993).

Hulme, et al., "The Role of Charge Interactions in Muscarinic Agonist Binding, and Receptor–Response Coupling," *Life Sciences,* 56(11/12):891–898 (1995) (Elsevier Science, Ltd., Editors).

Jacobi, et al., "Bis Heteroannulation. 2. Oxazole Alcohols from the Interaction of Lithiomethyl Isocyanide with Lactones. A Novel Synthesis of Evodone,", *J. Org. Chem.,* 46:2065–2069 (1981).

Jacobson, et al., "Molecular Probes fro Muscarinic Receptors: Functionalized Congeners of Selective Muscarinic Antagonists," *Life Sciences,* 56(11/12):823–830 (1995) (Elsevier Science, Ltd., Editors).

Jaen, et al., "In Vitro and In Vivo Evaluation of the Subtype–Selective Muscarinic Agonist PD 151832," *Life Sciences,* 56(11/12):845–852 (1995) (Elsevier Science, Ltd., Editors).

Janson, et al., "Chronic nicotine treatment partly protects against the 1–methyl–4–phenyl–2,3,6–tetrahydropyridine–induced degeneration of nigrostriatal dopamine neurons in the black mouse," *Acta Physiol. Scand.,* 132:589–591 (1988).

Janson, et al., "GM1 ganglioside protects against the 1–methyl–4–phenyl–1,2,3,6–tetrahydropyridine–induced degeneration of nigrostriatal neurons in the black mouse," *Acta Physiol. Scand.,* 132:587–588 (1988).

Jarvik, "Beneficial effects of nicotine," *Br. J. of Addiction* 86:571–575 (1991).

Jenden, et al., "Summary and Closing Comments," *Life Sciences,* 56(11/12):993–1000 (1995) (Elsevier Science, Ltd., Editors).

Jick et al., "Cigarette Smoking and Ulcerative Colitis," *N. Engl. J. Med.,* 308(5):261–263 (1983).

Julia and Paris, "Syntheses A L'Aide De Sulfones V$^{(+)}$–Methode De Synthese Generale de Doubles Liaisons," *Tetrahedron Letters,* 49:4833–4836 (1973).

Jung and Rohloff, "Intramolecular Diels–Alder Chemistry of Pyrroles," *J. Chem. Soc., Chem. Comm.* pp. 630–632 (1984).

Kaye and Soreff, "The Psychiatrist's Role, Responses, and Responsibilities When a Patient Commits Suicide," *Am. J. Psychiatry,* 148(6):739–743 (1991).

Kellar, "Epibatidine: Its Pharmacological Actions and Utility for Studying Neuronal Nicotinic Receptors," *Neurotransmissions,* XI(4):1–5 (1995).

Kilbinger, et al., "Prejunctional Muscarinic Receptors Regulating Neurotransmitter Release in Airways," *Life Sciences,* 56(11/12):981–987 (1995).

Kotsuki, H., et al., "High–Pressure Reactions of Pyrroles with Dimethyl Acetylenedicarboxylate," *Heterocycles,* 19:1915–1920 (1982).

Kricka and Vernon, "Nitrogen–Bridged Six–Membered Ring Systems: 7–Azabicyclo[2.2.1]hepta–2,5–dienes, Naphthalen–I,4–imines, and Anthracen–9,10–imines," *Adv. in Heterocycl. Chem.,* 16:87–121 (1974).

Krow, et al., "Homoepibatidines. syn–6– and syn–5(6–Chloro–3–pyridyl)isoquinuclidines. Potent Nicotinic Receptor Ligands," *Tetrahedron Letters* (In Press 1996).

Kuhar, M.J., et al. "3–β–(4–iodophenyl–tropan–2–β–carboxylic acid methyl ester tartrate and Related Compounds as Cocaine Receptor–Binding Ligands," *Chem. Abst.,* 116(7):447 (1992) 55131n.

Lambrecht, et al., "The Design and Pharmacology of Novel Selective Muscarinic Agonists and Antagonists," *Life Sciences,* 56(11/12):815–822 (1995) (Elsevier Science, Ltd., Editors).

Larock and Johnson, "Palladium–catalysed Intermolecular Arylation and Alkenylation of Bicyclic Alkenes," *J. Chem. Soc. Chem. Comm.,* 1368–1370 (1989).

Lashner et al.,"Testing Nicotine Gum for Ulcerative Colitis Patients," *Digest. Dis. Sci.,* 35(7):827–832 (1990).

Lee, J.W. and Oh, D.Y., "Conversion of B–Oxo Sulfones into Acetylenic Sulfones," *Synlett,* pp. 290 (1990).

Li, et al., "The Analgesic Effect of Epibatidine and Isomers," *Bioorg. and Med. Chem. Letters,* 3:2759–2764 (1993).

Lichtensteiger, et al., "A Quantitative Correlation Between Single Unit Activity and Fluorescence Intensity of Dopamine Neurones in Zona Compacta of Substantia Nigra, as Demonstrated Under the Influence of Nicotine and Physostigmine," *Brain Res.,* 117:85–103 (1976).

McPherson, et al., "Resolution and in Vitro and Initial in Vivo Evaluation of Isomers of Iodine–125–Labeled 1–Azabicyclo[2.2.2]oct–3–yl a–Hydroxy–a–(1–iodo–1–propen–3–yl)–a–phenylacetate: A High–Affinity Ligand for the Muscarinic Receptor," *J. Med. Chem.,* 38:3908–3917 (1995).

Melchiorre, et al., "The Design of Novel Methoctramine–Related Tetraamines as Muscarinic Receptor Subtype Selective Antagonists," *Life Sciences,* 56(11/12):837–844 (1995) (Elsevier Science, Ltd., Editors).

Moll, "The Treatment of Post–Encephalitic Parkinsonism by Nicotine," *Brit Med. J.,* 1:1079–1081 (1926).

Moss et al., "Nicotine and Cannabinoids as Adjuncts to Neuroleptics in the Treatment of Tourette Syndrome and Other Motor Disorders," Life Sciences, 44:1521–1525 (1989).

Myers, W.H., et al., "Tautomerizations, Protonations, and Electrophilic Additions of $n^2$–Coordinated Pyrroles," J. Am. Chem. Soc., 114(14):5684–5692 (1992).

Numa et al., "Molecular Structure of the Nicotinic Acetylcholine Receptor," Cold Spring Harbor Symp. Quant. Biol., 48:57–69 (1983).

Onali and Olianas, "Bimodal Regulation of cyclic Amp by Muscarinic Receptors Involvement of Multiple G Proteins and Different Forms of Adenylyl Cyclase," Life Sciences, 56(11/12):973–980 (1995) (Elsevier Science, Ltd., Editors).

Orlek, et al., "Design and Synthesis of Novel Muscarinic Agonists Containing the 1,2,4–Triazine Ring as an Ester Bioisotere," Bioorgan. & Med. Chem. Letters, 4(12):1411–1414 (1994).

Peralta, "Dual Modulation of a Potassium Channel by the M1 Muscarinic and B2–Adrenergic Receptors," Life Sciences, 56(11/12):957–964 (1995).

Qian, C.; et al., "Epibatidine is a nicotinic analgesic," European J. Pharmacology, 250(3):R–13–14 (1993).

Qian, et al., "Acetylcholine Muscarinic Receptor Regulations of the RAS/RAF/MAP Kinase Pathway," Life Sciences, 56(11/12):945–949 (1995).

Qian, et al., "Effects of Epibatidine on Body Weight in Mice," Med. Chem. Res., 4:493–501 (1994).

Reavill, "Action of nicotine on dopamine pathways and implications for Parkinson's disease," Nicotine Psychopharmacology, (Wonnacott, et al., Editors, Oxford University Press, 9:307–340 (1990).

Rhodes and Thomas, "Nicotine Treatment in Ulcerative Colitis," Drugs, 49(2):157–160 (1995).

Russell, et al., "Theoretical Background and Clinical Use of Nicotine Chewing Gum," National Institute on Drug Abuse Research Monograph Series 110–130 (1985).

Sahley et al., "Antinociceptive Effects of Central and Systemic Administration of Nicotine in the Rat," Psychopharmacology, 65:279–283 (1979).

Sakamoto, T., et al., "A Facile Synthesis of Ethynyl–Substituted Six–Membered N–Heteroaromatic Compounds," Synthesis, pp. 312, (1983).

Sanberg et al., "Nicotine potentiates the effects of haloperidol in animals and in patients with Tourette syndrome," Biomedicine and Pharmacotherapy, 43:19–23 (1989).

Sauerberg, et al., "Muscarinic Agonists as Analgesics. Antinociceptive Activity Versus $M_1$ Activity: SAR of Alkylthio–TZTP's and Related 1,2,5–Thiadiazole Analogs," Life Sciences, 56(11/12):807–814 (1995) (Elsevier Science, Ltd., Editors).

Sawyer and Narayanan, "Deacylation of Alkyl Carbamates: Selective Deprotection of Secondary Amines," Syn. Comm., 13:135–138 (1983).

Schwarz, et al., "Mutations of Aspartate 103 in the Hm2 Receptor and Alterations in Receptor Binding Properties of Muscarinic Agonists," Life Sciences, 56(11/12):923–929 (1995).

Sheppard, et al., "3–(2–(3–Pyridinyl)thiazolidin–4–oyl)Indoles, a Novel Series of Platelet Activating Factor Antagonists," J. Med. Chem., 37:2011–2032 (1994).

Showell, et al., "L–696,986: A Functionally Selective and Potent Muscarinic $M_1$ Receptor Partial Agonist," Medicinal Chem. Res., 3:171–177 (1993).

Spande, et al., "Epibatidine: A Novel(Chloropyridyl) Azabicycloheptane with Potent Analgesic Activity from an Ecuadoran Poison Frog," Org. Chem. 5:332–335 (1992).

Spande, et al., "Epibatidine,: A Novel (Chloropyridyl) azabicycloheptane with Potent Analgesic Activity from an Ecuadoran Poison Frog," J. Am. Chem. Soc., 114:3475–3478 (1992).

Steinbach and Ifune, "How many kinds of nicotinic acetylcholine receptor are there?" Trends Neurosci., 12:3–6 (1989).

Stinson, S., "Osmium(III) Found to Disrupt Aromaticity," Chemical and Engineering News, pp. 27–30 (Nov. 1992).

Taylor, "Agents Acting at the Neuromuscular Junction and Autonomic Ganglia," The Pharmacological Basis of Therapeutics, (Goodman and Gilman, Editors, Pergamon Press, 9:166–186 (1990).

Thomsen, et al., "Preparation of B–Keto Sulfones from [(Phenylsulfonyl)methylene]dilithium and Acid Chlorides," J. Org. Chem., 53:906–907 (1988).

Tobin et al., "Cigarette Smoking and Inflammatory Bowel Disease," Gastroenterology, 93:316–321 (1987).

Toube, T.P., "1.9. Cycloaddition Reactions of Acylpyrroles and Their Derivatives," Pyrroles, Part 2, (Jones, R. A., ed.) John Wiley, New York, pp. 92–95 (1992).

Tripathi et al., "Nicotine–Induced Antinociception in Rats and Mice: Correlation with Nicotine Brain Levels," J. Pharmacol. Exp. Ther., 221(1):91–96 (1982).

Trost, B.M., et al., "Desulfonylation of Aryl Alkyl Sulfones," Tetrahedron Lett., pp. 3477–3478 (1976).

Tsukamoto, et al., "Synthesis and Structure–Activity Studies of a Series of Spirooxazodine–2,4–diones: 4–Oxa Analogues of the Muscarinic Agonist 2–Ethyl–8–methyl–2, 8–diazaspiro[4.5]decane–1,3–dione," J. Med. Chem., 36:2292–2299 (1993).

Volle, "Nicotinic Ganglion–Stimulating Agents," Pharmacology of Ganglionic Transmission, (Kharkevich, D.A., ed., Springer–Verlag, Berlin), Chapter 9, pp. 281–312 (1980).

Wani, M.C., et al., "Plant Antitumor Agents. IX. The Total Synthesis of dl–Camptothecin," J. Am. Chem. Soc., 94:3631–3632 (1972).

Ward, et al., "Functionally Selective $M_1$ Muscarinic Agonists. 3. Side Chains and Azacycles Contributing to Functional Muscarinic Selectivity among Pyrazinylazacyles," J. Med. Chem., 38:3469–3481 (1995).

Wess, et al., "Muscarinic Acetylcholine Receptors: Structural Basis of Ligand Binding and G Protein Coupling," Life Sciences, 56(11/12):915–922 (1995) (Elsevier Science, Ltd., Editors).

Williams, et al., "Neuronal Nicotinic Acetylcholine Receptors," Drug News & Perspectives 7(4):205–223 (1994).

* cited by examiner

EPIBATIDINE AND DERIVATIVES THEREOF AS NICOTINE CHOLINERGIC RECEPTOR AGONISTS

This application is a divisional application of U.S. Ser. No. 08/119,697, filed on Sep. 10, 1993 now abandoned.

BACKGROUND OF THE INVENTION

The present invention is directed to methods of treatment utilizing harmaceutical compositions comprising epibatidine and/or synthetic derivatives thereof, wherein the utility of the composition is based upon the fact that the active ingredients have been found to be nicotine receptor agonists. Epibatidine has the following structure:

(1)

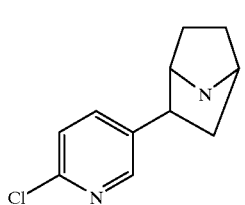

Epibatidine was first isolated by Daly et al. from skins of the Ecuadoran poison frog, *Epipedobates tricolor* (Daly, et al., *J. Am. Chem. Soc.*, 102: 830 (1980)). Its structure was determined by mass spectroscopy, infra red spectroscopy, and nuclear magnetic resonance as exo-2(6-chloro-3-pyridyl)-7-azabicyclo [2.2.1] heptane (1) (Spande, et al., *J. Am. Chem. Soc.*, 114: 3475 (1992)). This alkaloid has been shown to be a potent analgesic with a nonopioid mechanism of action. The analgesic effect of epibatidine was approximately 200-times higher than morphine using hot plate assay, and approximately 500-fold that of morphine in eliciting the Straub-tail response. The epibatidine-induced analgesia was not blocked by the opioid receptor antagonist naloxone. Furthermore, it has been determined that epibatidine had a negligible affinity for opioid receptor (⅛₀₀₀ times that of morphine). See, Spande, et al., *J. Am. Chem. Soc.*, 114: 3475 (1992). The mechanism of epibatidine-induced analgesia is unknown.

The present inventors have discovered that epibatidine and synthetic analogs thereof (see, Fei and Shen, *Tet. Let.*, 34: 4477 (1993); Fletcher, et al., *J. Chem. Soc. Chem. Comm.*, p. 1216 (1993) and Broka, *Tet. Let.*, 34:3251 (1993)), possess another unique and unexpected utility, one which presents the ability to treat or ameliorate disease states or conditions, not commonly associated with analgesia. Thus, the present invention is directed to methods of treatment based upon the use of epibatidine and its analogs as nicotine receptor agonists.

The present invention demonstrates that epibatidine is the third natural alkaloid nicotinic receptor agonist. The other two natural alkaloids are nicotine, first isolated from leaves of tobacco in 1828, and lobeline, first isolated from *Lobelia inflata* (India tobacco) in 1915. See, Taylor, in *Goodman and Gilman's The Pharmacological Basis of Therapeutics*, 18th Ed., Gilman et al., eds., Pergamon Press, pp. 166–186 (1990).

Nicotine is a central nervous system (CNS) and ganglionic nicotinic receptor agonist and has been found to exert a potent analgesia on thermal stimuli as measured by the hot-plate or tail-flick test in both rats and mice (Tripathi, et al., *J. Pharmacol. Exp. Therap*, 221: 91 (1982); Sahley et al., *Psychopharmacology*, 65: 279 (1979); Cooley, et al., *Pharmacol. Biochem. Behav.*, 36: 413 (1990); Christensen, et al., *J. Neural. Transm. GenSec.*, 80: 189 (1990)).

SUMMARY OF THE INVENTION

One object of the present invention is to provide pharmaceutical compositions comprising as the active ingredient, epibatidine and/or derivatives thereof, useful as nicotinic agonists. Another object of the present invention is to provide pharmaceutical compositions and new methods of treatment which replace nicotine in the treatment of certain disease states or conditions, including movement disorders such as Parkinson's disease, Tourette's syndrome, and the like, Alzheimer's disease, ulcerative colitis and aphthous ulcer, and in other medical uses, e.g., smoking cessation and body weight loss.

As such, the present invention provides pharmaceutical compositions useful as a nicotine agonist, said compositions comprising an effective nicotine agonist amount of a 7-azabicyclo[2.2.1]-heptane or heptene compound having formula (2):

(2)

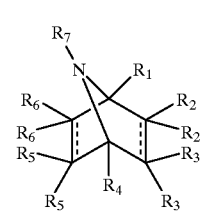

wherein:

$R^1$ and $R^4$ are independently selected from the group consisting of hydrogen, alkyl, including —$CH_3$; alkylhydroxy, including —$CH_2OH$; alkyloxyalkyl, including —$CH_2OCH_3$; alkylthioalkyl, including —$CH_2SCH_3$; alkylamino, including —$CH_2NHCH_3$ and —$CH_2N(CH_3)_2$; oxyalkyl, including —$OCH_3$; carboalkoxy, including carbomethoxy; allyl; aryl; heteroaryl such as pyridine or substitutes of pyridine, thioalkyl, including —$SCH_3$, and Q (defined below);

each $R^3$, $R^5$ and $R^6$ may be independently selected from the group consisting of hydrogen, alkyl, including —$CH_3$; alkylhydroxy, including —$CH_2OH$; alkyloxyalkyl, including —$CH_2OCH_3$; alkylthioalkyl, including —$CH_2SCH_3$; alkylamino, including —$CH_2NH_2$; alkylaminoalkyl or alkylaminodialkyl, including —$CH_2NHCH_3$ and —$CH_2N(CH_3)_2$; oxyalkyl, including —$OCH_3$; thioalkyl, including —$SCH_3$; halo, including —Cl; —$CF_3$; —$NH_2$; alkylamino or dialkylamino, including —$N(CH_3)_2$ and —$NHCH_3$—$CO_2H$; —$CO_2$-alkyl, including —$CO_2CH_3$; —C(O)-alkyl, including —C(O)$CH_3$; —CH; —C(O)$NH_2$; —C(O)NH(alkyl); —C(O)N(alkyl)$_2$, including —C(O)N($CH_3$)$_2$; allyl; and —$SO_n$(alkyl), —$SO_n$(aryl), —$SO_n$(heteroaryl), wherein n=0, 1, or 2;

$R^5$ and $R^6$ together can be alkylidene or haloalkylidene, including —$CH_2$— and —$CF_2$—;

each $R^2$ may be independently selected from the group consisting of hydrogen, alkyl, including —$CH_3$; —$CH_2$—; HC=$CH_2$; alkylhydroxy, including —$CH_2$—OH; alkyloxyalkyl, including —$CH_2O$—(alkyl); alkylamine, including —$CH_2NH_2$; carboxylate, —CN; —Q; —C(O)Q; and -alkyl(Q);

wherein Q is selected from the group consisting of:

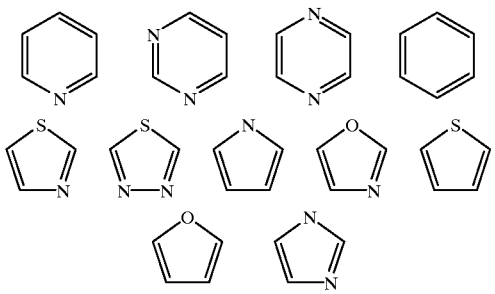

and wherein the Q moiety can be optionally substituted with from 1 to 3 substituent groups W;
  wherein each substituent group W is selected from the group consisting of alkyl, including —$CH_3$; halo, including —Cl, —Br and —F; aryl; heteroaryl; —OH; oxyalkyl, including —$OCH_3$; —SH; thioalkyl, including —$SCH_3$; —SO(alkyl), including —$SOCH_3$; —$SO_2$alkyl, including —$SO_2CH_3$; —$OCH_2CH=CH_2$; —$OCH_2(C_6H_5)$; —$CF_3$; —CN; alkylenedioxy, including methylenedioxy; —$CO_2H$; —$CO_2$alkyl, including —$CO_2CH_3$; —$OCH_2CH_2OH$; —$NO_2$; —$NH_2$; —NH(alkyl), including —$NHCH_3$; —N(alkyl)$_2$, including —N(CH$_3$)$_2$; —NCH(O)alkyl, including —NHC(O)CH$_3$; —$SO_2CF_3$; and —$NHCH_2$aryl, including —$NHCH_2(C_6H_5)$;
  $R^7$ is selected from the group consisting of hydrogen; alkyl, including —$CH_3$; —$CH_2$-(cycloalkyl), including —$CH_2$-(cyclopropyl); —$CH_2CH=CH_2$; —$CH_2CH_2(C_6H_5)$; alkylhydroxy, including —$CH_2CH_2OH$; alkylamino(alkyl)$_{0-2}$, including —$CH_2CH_2N(CH_3)_2$; alkoxyalkyl; alkylthioalkyl; and aryl;
wherein the lines—represent optional double bonds in the formula;
and a pharmaceutically acceptable carrier, excipient or diluent.
As used herein, the following definitions apply:
  Alkyl means a $C_1$ to $C_{30}$, preferably a $C_1$ to $C_{20}$, straight or branched group. Lower alkyl means a $C_1$ to $C_{12}$, preferably a $C_1$ to $C_6$ group. Typical $C_1$–$C_6$ alkyl groups include methyl, ethyl, n-propyl, i-propyl, n-butyl, t-butyl, i-butyl, pentyl and hexyl groups.
  Cycloalkyl means a $C_3$ to $C_{12}$, preferably a $C_3$ to $C_8$ cyclic group. Typical $C_{3-8}$ cycloalkyl groups include cyclopropyl, cyclobutyl, cyclopentyl, cyclohexyl, cycloheptyl, and cyclooctyl groups.
  Typical $C_2$–$C_6$ carboxylic acyl groups include acetyl, propanoyl, i-propanoyl, butanoyl, s-butanoyl, pentanoyl and hexanoyl groups.
  Typical aryl groups include phenyl, naphthyl, phenanthryl, anthracyl and fluorene groups.
  Typical aryl-substituted carboxylic acid groups include the above-mentioned carboxylic acyl groups substituted by one or more aryl groups, e.g., diphenylacetoxy and fluorenecarboxy groups.
  Typical alkaryl groups include the above-listed aryl groups substituted by one or more $C_1$–$C_6$ alkyl groups.
  Typical aralkyl groups include a $C_1$–$C_6$ alkyl group substituted by one of the above-listed aryl groups, e.g., phenethyl, phenylpropyl, phenylbutyl, phenylpentyl and phenylhexyl groups as well as the branched chain isomers thereof.
  Typical $C_1$–$C_6$ alkoxycarbonyl groups include carbonyl substituted by methoxy, ethoxy, propanoxy, i-propanoxy, n-butanoxy, t-butanoxy, i-butanoxy, pentanoxy, and hexanoxy groups.

Typical aralkyl groups include the above-listed $C_1$–$C_6$ alkyl groups substituted by phenyl, naphthyl, phenanthryl, and anthracyl groups.
  Typical $C_2$–$C_5$ alkenyl groups include vinyl, allyl, 2-butenyl, 2-pentenyl, and 2-hexenyl groups.
  Typical $C_2$–$C_8$ alkynyl groups include acetynyl and propargyl groups.
  Typical halo groups include fluorine, chlorine, bromine and iodine.
  Typical aroyl groups include carbonyl substituted by phenyl, naphthyl, phenanthryl, and anthracyl groups.
  Typical aralkanoyl groups include carbonyl substituted by the above-listed aralkyl groups.
  Typical aralkoxy groups include the above listed $C_1$–$C_6$ alkoxy groups substituted by phenyl, naphthyl, phenanthyl, and anthracyl groups.
  Typical substituted aryl groups include the above-listed aryl groups substituted by halo, hydroxy, $C_1$–$C_6$ alkoxy, amino, and the like.
  Typical heteroaryl groups include furyl, thienyl, pyrrolyl, thiazolyl, pyridyl, pyrimidinyl, pyrizinyl, oxazolyl and phthalimido groups which may be fused to a benzene ring.
  Typical substituted heteroaryl groups include the above-listed heteroaryl groups substituted by halo, $C_1$–$C_6$ alkyl and the like.
  Typical $C_5$–$C_6$ heterocycloalkyl groups include tetrahydrofuranyl, tetrahydropyranyl, piperidinyl, piperazinyl, morpholino and pyrrolidinyl groups.
  Additional substituent groups for the above include halogen, hydroxy, $CF_3$, $C_1$–$C_6$ acyl, $C_1$–$C_6$ alkyl, $C_2$–$C_6$ alkenyl, $C_2$–$C_6$ alkynyl, $C_1$–$C_6$ alkoxy, $C_6$–$C_{18}$ aryl, $C_2$–$C_6$ dialkoxymethyl, cyano, $C_3$–$C_6$ cycloalkyl, $C_3$–$C_6$ heterocycloalkyl, $C_3$–$C_{15}$ dialkylaminoalkyl, carboxy, $C_2$–$C_6$ carboxylic acid, carboxamido, $C_1$–$C_6$ haloalkyl, $C_1$–$C_6$ haloalkylthio, allyl, $C_7$–$C_{20}$ aralkyl, a $C_3$–$C_6$ heterocycloalkyl ring fused to a benzene ring, $C_1$–$C_6$ alkylthio, $C_1$–$C_6$ alkylsulfonyl, $C_1$–$C_6$ haloalkylsulfonyl, $C_1$–$C_8$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro, $C_2$–$C_{15}$ dialkylsulfamoyl, and the like.
  The present invention will be appreciated more completely by those having ordinary skill in this art upon consideration of the detailed description of the invention, which is provided below.

DETAILED DESCRIPTION OF THE PREFERRED EMBODIMENTS

As described above, the present invention is directed to methods of treatment utilizing pharmaceutical compositions comprising an effective nicotine agonist amount of epibatidine (1):

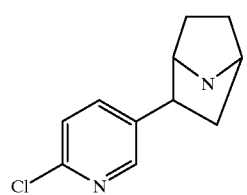

and/or synthetic derivatives thereof, which are represented by Formula (2) shown above. The present inventors have discovered that, in addition to the potent analgesic activity previously reported for epibatidine and its synthetic analogs, these compounds surprisingly and unexpectedly have high activity as nicotine receptor agonists. As detailed herein below, this activity makes these compounds useful for the treatment of a wide variety of aliments, including Parkinson's disease, Tourettes's Syndrome, Alzheimer's disease, ulcerative colitis, aphthous ulcer, cessation of smoking and body weight loss.

Differences in responses mediated by acetylcholine result from actual differences in cholinergic receptors. Responses evoked by acetylcholine are described as being nicotinic or muscarinic, which have led to the subclassification of cholinergic receptors as nicotinic cholinergic receptors or muscarinic cholinergic receptors. The response of most autonomic effector cells in peripheral visceral organs is typically muscarinic, whereas the response in parasympathetic and sympathetic ganglia, as well as responses of skeletal muscle, is nicotinic. The nicotinic receptors of autonomic ganglia and skeletal muscle are not homogenous because they can be blocked by different antagonists. Thus, d-tubocurarine effectively blocks nicotinic responses in skeletal muscle, whereas hexamethonium and mecamylamine are more effective in blocking nicotinic responses in autonomic ganglia, thereby confirming heterogeneity in nicotinic cholinergic receptors (named $N_M$ and $N_N$ receptor respectively).

Muscarinic receptors may also be divided into at least two subtypes, $M_1$ and $M_2$. In general, muscarinic cholinergic receptors with the pharmacological profile characteristic of the $M_1$ subtype are found in autonomic ganglia and in the CNS, whereas $M_2$ muscarinic receptor exist at neuroeffector junctions of organs innervated by the parasympathetic system.

Nicotinic receptors are ligand-gated ion channels, and their activation always causes a rapid increase in cellular permeability to $Na^+$ and $K^+$, depolarization, and excitation. The primary structures of various species of nicotine receptor (Numa et al., *Cold Spring Harbor Symp. Quant. Biol.*, 48: 57 (1983)) have been deduced by molecular cloning. The nicotinic receptors are pentameric proteins that are composed of at least two distinct subunits. Each subunit contains multiple membrane-spanning regions, and the individual subunits surround an internal channel. One of the subunits (designated α) is present in at least two copies and forms the ligand binding site on the receptor. Heterogeneity of the nicotinic receptors was further revealed by molecular cloning.

Nicotinic receptors ($N_N$) in the CNS also exist as pentamers, they are composed of only two subunits, α and β. Further complexity arises because multiple forms of α and β have been detected (Steinbach and Ifune, *Trends Neurosci.*, 12: 3 (1989)). In general, each of the α and β subunits is found in discrete regions of the brain.

Drugs that stimulate cholinergic receptor sites on autonomic ganglia can be grouped into two major categories. The first group consists of drugs with nicotinic specificity, including nicotine itself. Their excitatory effects on ganglia are rapid in onset, are blocked by nondepolarizing ganglionic blocking agents, and mimic the initial excitatory postsynaptic potential (EPSP). The second group is composed of agents such as muscarine and methacholine. Their excitatory effects on ganglia are delayed in onset, blocked by atropine-like drugs, and mimic the slow EPSP.

Ganglionic blocking agents impair transmission by actions at the primary nicotinic receptors and also may be classified into two groups. The first group includes those drugs that initially stimulate the ganglia by an ACh-like action then block them because of a persistent depolarization (e.g., nicotine); prolonged application of nicotine results in desensitization of the cholinergic receptor site and continued blockade (Volle, in: *Pharmacology of Ganglionic Transmission.* Kharkevich, D. A., ed. Springer-Verlag, Berlin, pp. 281–312, 1980). The blockage of autonomic ganglia by the second group of blocking drugs, of which hexamethonium and trimethaphan can be regarded as prototypes, does not involve prior ganglionic stimulation or changes in the ganglionic potentials. These agents impair transmission either by competing with ACh for ganglionic cholinergic receptor sites or by blocking the channel when it is open, therefore, the initial EPSP is blocked and ganglionic transmission is inhibited.

Parkinsonism is a clinical syndrome comprised of four cardinal features: bradykinesia, muscular rigidity, resting tremor, and abnormalities of posture and gait. Despite advances in the understanding of the pathophysiology and the treatment of parkinsonism, its cause remains unknown. Now-classical investigations performed in the 1950's and 1960's clearly established the basal ganglia of the brain and specifically the nigrostriatal dopaminergic system as the site of the fundamental lesion in Parkinson's disease. Abundant evidence suggests that parkinsonism is a syndrome of deficiency in the dopaminergic innervation of the basal ganglia owing to degeneration of neurons in the substantia nigra (Ehringer and Hornykiewicz et al., *Klin. Wochenschr,* 38: 1236 (1960)). Since dopamine does not cross the blood-brain barrier when administered systemically, it has no therapeutic effects in parkinsonism. However, levodopa, the immediate metabolic precursor of dopamine, is transported into the brain and permeates into striatal tissue, where it is decarboxylated to dopamine. Clinical studies demonstrated the value of replenishment of depleted stores of dopamine in parkinsonism.

Among the panoply of other neurotransmitters contained in the basal ganglia, acetylcholine is currently known to be of significance in the pharmacotherapy of parkinsonism. A simplistic, but useful, neurochemical model of the function of the basal ganglia suggests that the neostriatum (caudate nucleus and putamen) normally contains balanced inhibitory dopaminergic and excitatory cholinergic components (Duvoisin, *Arch. Neurol.,* 17: 124 (1967)). Although cholinergic neurons are not damaged in Parkinson's disease, the decrease in dopaminergic activity results a relative excess of cholinergic influence. Consequently, a second strategy for the treatment of parkinsonism is to block cholinergic activity in an attempt to restore the balance of dopaminergic and cholinergic tone in the striatum. Furthermore, dopaminergic agonists and cholinergic (muscarinic) antagonists are often combined effectively.

Many epidemiology reports have found that smokers are less likely to develop Parkinson's disease than non-smokers. Evidence supporting a possible protective role for nicotine are the findings of Janson et al., *Acta Physisologica Scandinavica,* 132: 589 (1988) that pretreatment with nicotine will prevent some of the damage to the extra-pyramidal system by the illicit drug MPTP which produces a Parkinson-like syndrome in human. Another movement disorder, Tourette's syndrome, seems to be responsive to nicotine (Devor and Isenberg, *Lancet,* 2: 1046 (1989)). Sanberg et al., *Biomedicine and Pharmacotheraphy,* 43: 19 (1989) and Moss et al., *Life Sciences,* 44: 1521 (1989) found that nicotine potentiated the therapeutic effects of haloperidol in patients with Tourette's syndrome. They also found that nicotine would potentiate haloperidol-induced hypokinesia in rats.

The mechanism of action of nicotine in movement disorder is unknown. Development of tolerance to nicotine was found in humans. It was reported that tachyphylaxis developed to nicotine-induced antinociception in rats (1.25 mg/kg, s.c.) within 10 min lasted for up to 14 hr, but tachyphylaxis did not develop to nicotine-induced antinociception in mice (3 mg/kg, s.c.). (Tripathi, et al., *J. Pharmacol. Exp. Ther.*, 22: 91 (1982)). Since the antinociception of nicotine is mediated through central nicotinic receptor, the mechanism of nicotine-induced desensitization of ganglionic nicotinic receptor may explain the development of tachyphylaxis to central nicotine. Nicotine initially stimulates the ganglia by an ACh-like action, as indicated by a transient tremor, then blocks them because of a persistent depolarization (Volle, in: *Pharmacology of Ganglionic Transmission*, Kharkevich, D. A., ed., Springer-Verlag, Berlin, pp. 281–312, 1980). Furthermore, one can apply the same mechanism to elucidate the therapeutic effects of nicotine in movement disorders. Smoking or exposure to nicotine induces a persistent depolarization of cholinergic neurons in stratum, which markedly lessens or induces the loss of the response to the ACh transmitter, leading to a blockage of cholinergic activity. In addition, a large number of observations indicate that nicotine can enhance dopamine release via nicotinic-cholinergic receptors located on the dopaminergic nerve terminals. This change is correlated with an increase in the fluorescence intensity of dopamine within the *zona compacta* of *substantia nigra* (Lichtensteiger, et al., *Brain Res.*, 117, 85, (1976)). Nicotine, continuously administered via subcutaneously implanted minipumps, can exert protective effects on the nigrostriatal dopaminergic neurons as an increased number of dopaminergic nerve cell bodies seemed to survive. It has been hypothesized that these protective effects of nicotine are due to a desensitization of the nicotinic-cholinergic receptors on the dopamine neurons, leading to a reduced firing rate, improved ionic homeostasis and thus to reduced energy demands (Janson, et al., *Act. Physiol. Scand.*, 132: 589 (1988); Reavill, in *Nicotine Psychopharmacology*, Wonnacott, et al., eds., Oxford University Press, pp. 307 (1990)). A putative anti-Parkinsonian action of nicotine and smoking may be due at least in part to a release action of nicotine on dopaminergic nerve terminals.

The therapeutic effects of nicotine in Parkinson's disease was found more than half century ago (Moll, *Brit. Med. J.*, 1: 1079 (1926)). Besides parkinsonism, nicotine was employed as a potential drug in the treatment of Tourette's Syndrome (another movement disease) (McConville et al., *Am. J. Psychiatry*, 148: 739 (1991)), ulcerative colitis (Jick et al., *N. Engl. J. Med.*, 308: 261 (1983); Tobin et al., *Gastroenterology*, 93: 316 (1987), Lashner et al., *Digest. Dis. Sci.*, 35: 827 (1990), aphthous ulcers (Bittoun, *Med. J. Australia*, 154: 471 (1991)), smoking cessation (Glassman and Covey, *Drugs*, 40: 1 (1990); Gourlay and McNeil, *Med. J. Australia*, 153: 699 (1990)), and body weight loss/gain (Grunberg et al., *Psychopharmacology*, 83: 93 (1984)). The therapeutic effects of nicotine were reviewed by Jarvik (*Brit. J. Addict.*, 86: 571 (1991)). Agonists and antagonists of nicotine useful as smoking deterrents are reported in U.S. Pat. No. 4,966,916 (Abood, 1990). Nicotine has not generally been used as a clinical drug, particularly due to its toxicity and its low potency in the treatment of disease states including parkinsonism and other movement disorders.

Development of drugs providing a more selective, more potent and more persistent depolarization of cholinergic neurons in CNS than nicotine will provide a new method for the treatment of Parkinson's disease and other movement disorders. Epibatidine and its synthetic derivatives have been found to satisfy these criteria. The supporting evidence for this conclusion includes the following:

1. Epibatidine at approximately 1/100th the dose of nicotine (<10 $\mu$g/kg) mimicked nicotine-induced analgesia, hyperventilation, and tremor; with somewhat larger doses (>20 $\mu$g/kg), the tremor is followed by convulsion and death results from failure of respiration. Since the analgesic dose of nicotine is 10–50 times higher than its therapeutic dose (Reavill, in *Nicotine Psychopharmacology*, Wonnacott, et al., eds., Oxford University Press, pp. 307, (1990)), the satisfactory therapeutic effects may be achieved by the very potent nicotine receptor agonist epibatidine at hundreds of ng to a few $\mu$g per kg. In this low dose range, epibatidine may not induce the undesired CNS effects that nicotine induces. When a higher dose of epibatidine is needed, these CNS responses to epibatidine could be avoided by a low starting dose, followed by a high dose a few minutes after the first dose;

2. The pretreatment with mecamylamine (a central non-depolarizing nicotinic blocker) at a very low dose completely blocked epibatidine-induced analgesia and other CNS responses;

3. The opioid antagonist naloxone and the $\alpha$-2 adrenoceptor antagonist yohimbine blocked nicotine-induced analgesia (Tripathi et al., *J. Pharmacol. Exp. Ther.*, 221: 91 (1982)), but did not antagonize epibatidine-induced analgesia; and 4. Tachyphylaxis developed to epibatidine was much higher and longer than that developed to nicotine in both rats and mice.

Based upon these results, the present inventors have concluded that epibatidine and its synthetic derivatives represent novel, potent, and long-acting nicotinic receptor agonists, which will be effective in the treatment, prevention, or amelioration of the disease states and/or medical conditions described above.

The pharmaceutical composition of the present invention may be administered for therapy by any suitable route including oral, rectal, nasal, topical (including buccal and sublingual), vaginal and parenteral (including transdermal, subcutaneous, intramuscular, intravenous and intradermal). It will be appreciated that the preferred route will vary with the condition and age of the recipient, the nature of the condition and the active ingredients.

In general a suitable dose for each of the above-mentioned conditions (e.g., Parkinson's disease, Tourette's syndrome, etc.) will be in the range of from about 0.1 to 20 $\mu$g per kilogram body weight of the recipient (e.g., a human) per day, preferably in the range of from about 0.5 to 2 $\mu$g per kilogram body weight per day and most preferably in the range of from about 1 to 2 $\mu$g per kilogram body weight per day. The desired dose is preferably presented as two, three, four, five, six or more sub-doses administered at appropriate time intervals throughout the day. These sub-doses may be administered in unit dosage form, for example, containing from about 0.05 to 5 $\mu$g, preferably from about 0.25 to 1.5 $\mu$g, and most preferably from about 0.5 to 1 $\mu$g of active ingredient per unit dosage form.

Ideally, the active ingredient should be administered to achieve peak plasma concentrations of the active ingredient of from about 0.2 to 30 ng/ml, preferably from about 1 to 15 ng/ml, most preferably about 2 to 10 ng/ml. This may be achieved, for example, by the intravenous injection of a 0.1 to 5% solution of the active ingredient, optionally in saline, or orally administered as a bolus containing about 0.2 to 50 $\mu$g/kg of the active ingredient. Desirable blood levels may be maintained by continuous infusion to provide about 0.005 to 2 $\mu$g/kg/hour or by intermittent infusions containing about 0.1 to 5 $\mu$g/kg of the active ingredient.

While it is possible for the active ingredient to be administered alone, it is preferable to present it as a pharmaceutical formulation. The formulations of the present invention comprise the active ingredient, as defined above, together with at least one pharmaceutically acceptable carrier, diluent or excipient. Preferred formulations include those adapted for oral, rectal, nasal, topical (including buccal and sublingual), vaginal or parenteral (including subcutaneous, intramuscular, intravenous and intradermal) administration. The formulations may conveniently be presented in unit dosage form and may be prepared by methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention adapted for oral administration may be presented as discrete units such as capsules or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked providone, cross-linked sodium carboxymethyl cellulose) surface-active or dispersing agent.

Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl-methyl cellulose in varying proportions to provide the desired release profile. Tablets may optionally be provided with an enteric coating, to provide release in parts of the gut other than the stomach.

Formulation adapted for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations adapted for rectal administration may be presented as a suppository with a suitable base comprising for example cocoa butter or salicylate.

Formulations adapted for vaginal administration may by presented as pessaries, tampons, creams, gels, pasted, foams or spray formulations containing in addition to the active ingredient such carriers as are known in the art to be appropriate.

Formulations adapted for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be present in unit-dose or multi-dose sealed containers, for example, ampules and vials, and any be stored in a freeze-dried (lyophilized) condition requiring only the addition of the sterile liquid carrier, for example water for injections, immediately, prior to use. Extemporaneous injection solutions and suspensions any be prepared from sterile powders, granules and tablets of the kind previously described.

Preferred unit dosage formulations as those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agent.

The present invention will be further illustrated with reference to the following examples which will aid in the understanding of the present invention, but which are not to be construed as limitations thereof. All percentages report herein, unless otherwise specified, are percent by weight. All temperatures are expressed in degrees Celsius.

EXAMPLES

Animals:

Female and male CD-1 mice (20–25 g) and male CD-1 rats (300–400 g) were obtained from Charles River Labs (Wilmington, Mass.). Rats were housed in groups of two and mice were housed in group of five. All animals had free access to tap water and chow pellets in a thermostatically-controlled room temperature (20° C.) on a 12 hr light/dark cycle.

Antinociceptive activity of epibatidine and derivatives:

After the control values were measured, the antinociceptive activity of various epibatidine isomers and derivatives (n-5/group) was tested 5 min after s.c. injection.

The antinociceptive activity of epibatidine isomers and derivatives is summarized in Table 1. The r-(CMI-545), d-(CMI-488) and l-epibatidine (CMI-477) all showed very high potency with $ED_{50}$ of 10, 7 and 9 $\mu g/kg$, respectively.

Duration of epibatidine- or nicotine induced antinociception:

Duration of l-epibatidine- or nicotine-induced antinociception was assessed in mice by measuring antinociception at 2, 5, 10, 20 min after l-epibatidine (20 $\mu g/kg$, s.c.) or nicotine (5 mg/kg, s.c.).

Nicotine (5 mg/kg) and l-epibatidine (20 $\mu g/kg$) produced a decrease in responsiveness to radiant heat in the tail-flick test. A Friedman's analysis of variance test revealed that the drug effect was significant ($P<0.05$). The onset of action was rapid with maximum antinociception occurring with 2 min for nicotine and 5 min for l-epibatidine. The duration of antinociception for l-epibatidine was about 20–30 min and for nicotine within 10 to 20 min.

Antagonism of epibatidine antinociception in mice:

Mice (seven per group) were pretreated i.v. with either 0.9% saline or one antagonist (mecamylamine, hexamethonium, atropine, naloxone or yohimbine) 10 min before administration of l-epibatidine or nicotine at different doses. A control response (1.5–4 sec.) was determined for each animal before treatment and test latencies were assessed at 5 min. after l-epibatidine administration (s.c., 5 ml/kg) or 2 min after nicotine (s.c., 5 ml/kg). The $ED_{50}$ values were calculated using the PC software, GraphPad InPlot (ver 3.0).

Various drugs were tested for antagonism of epibatidine at a high dose (20 $\mu g/kg$) and the results are contained in Table 2. l-Epibatidine-induced antinociception, as measured by the tail-flick test, was completely blocked by pretreatment with the centrally active nicotine receptor blocker mecamylamine at a low dose (1 mg/kg), but was not significantly affected by the opiate-receptor antagonist naloxone up to 3 mg/kg. Quaternary nicotine receptor blocker hexamethonium (3 mg/kg), which passes only poorly into the central nervous system (Taylor, in *Goodman and Gilman's The Pharmacological Basis of Therapeutics*, 18th Ed., Gilman et al. Eds., Pergamon Press, pp 166–186 (1990)) 1957), showed less potent antagonism of l-epibatidine than did the corresponding tertiary antagonist mecamylamine. Large dose of yohimbine (an $\alpha_2$ adrenergic antagonist) was less effective, and atropine (M receptor antagonism) was inactive in antagonizing l-epibatidine antinociception.

A dose-response relationship was established in mice for both nicotine and l-epibatidine by measuring antinociception at the time of maximal effects. Two minutes after nicotine administration (s.c.), the $ED_{50}$ was found to be 1.4 mg/kg, whereas 5 min after l-epibatidine administration (s.c.) the $ED_{50}$ was determined to be 13.6 µg/kg. A dose of nicotine or epibatidine as high as the $ED_{50}$ produces tremors and sedation in most animals with much higher doses (nicotine $\geq$ 5 mg/kg, epibatidine $\geq$ 20 µg/kg) the tremor was followed by convulsion and death in some animals within 10 min after injection. Furthermore, in the animals pretreated with mecamylamine (1 mg/kg, i.v.) the dose-responses for either l-epibatidine or nicotine was measured. The potency ratio (i.e., $ED_{50}$ with blocker/$ED_{50}$ without blocker) for l-epibatidine and nicotine was found as high as 21.5 and 24.6, respectively.

Also, the antinociception of d-epibatidine was completely abolished by the nicotinic receptor antagonist mecamylamine, but it was not affected by the opioid receptor antagonist naloxone.

Effects of l-epibatidine and nicotine on respiration and blood pressure in rats, and the blockage thereof by mecamylamine:

Rats were anesthetized by sodium pentobarbital (50 mg/kg, i.p.) and body temperature of the animals was maintained by a Harvard homeothemic blanket (Harvard Apparatus, Edenbridge, KE) at 37° C. during these experiments. A polyethylene catheter (PE50) was inserted into the left common carotid artery. A polyethylene tubing (PE240) was inserted into the trachea and connected to a Fleisch 3.0 pneumotachograph (Whittaker, Blue Bell, Pa.), which was coupled to a Validyne DP45-14 differential pressure transducer (Validyne, Northride, Calif.). Another PE 190 tubing was placed into esophagus. Transpulmonary pressure, as the difference between the tracheal and esophageal pressure, was detected by a Validyne MPXIIDP differential transducer. The mean blood pressure (MBP) and the heart rates (HR) were derived from the input signal of blood pressure. The respiratory parameters, including tidal volume ($V_T$), respiratory frequency (RF), minute volume ($V_E$), lung resistance ($R_L$) and dynamic lung compliance ($C_{dyn}$) were derived from the input signals of flow and the transpulmonary pressure. These data were captured by a Buxco LS-20 system with a $PC_{486}$ computer.

Rats (3–4/group) were pretreated with either 0.9% saline (1 ml/kg, i.p.) or mecamylamine (1 mg/kg, i.p.) 10 min before administration of l-epibatidine (10 µg/kg, s.c.) or nicotine (2 mg/kg, s.c.). Blood pressure, heart rate, and pulmonary functions were monitored during whole experiment.

After nicotine administration (2 mg/kg, s.c.) in anesthetized rats, the cardiovascular and pulmonary responses included hypertension or biphase changes of blood pressure, depressed breath frequency, and increased tidal volume. Epibatidine (10 µg/kg, s.c.) mimicked these nicotine-induced changes. Mecamylamine (1 mg/kg, i.p.) also blocked l-epibatidine-induced respiratory responses and changes in blood pressure.

Development of tachyphylaxis:

The tachyphylaxis was assessed in mice by pretreatment with either l-epibatidine (15 µg/kg s.c.) or nicotine (5 mg/kg s.c.) at either 10 min, 3 or 16 h (N=7 per group) before a secondary injection. The mice were tested for antinociception 5 min after epibatidine administration and 2 min after administration of nicotine.

The animals receiving nicotine twice at 3 hr intervals showed no tachyphylaxis, whereas those receiving l-epibatidine at both 3 hr and 16 hr intervals developed tachyphylaxis.

TABLE I

Analgesic Effects of Epibatidine and Derivatives in the Tail-Flick Assay in Mice

| Compound | Dose Range (µg/kg, s.c.) | $ED_{50}$ at 5 min (µg/kg) |
|---|---|---|
| CMI-488 (d-1) | 5–50 | 7 |
| CMI-489 (r-4) | 10–50 | 9 |
| CMI-477 (l-1) | 5–50 | 9 |
| CMI-545 (r-1) | 5–50 | 10 |
| CMI-526 | 50–200 | 127 |
| CMI-495 | 100–500 | 285 |
| CMI-492 | 500–1000 | 726 |

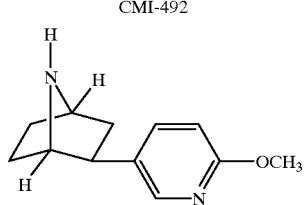

CMI-492

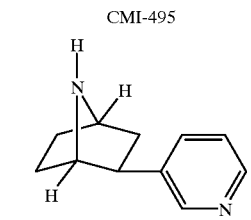

CMI-495

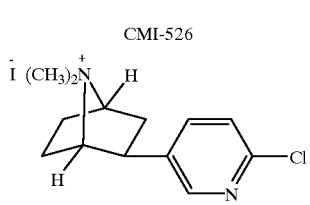

CMI-526

CM1-545

TABLE I-continued

Analgesic Effects of Epibatidine and Derivatives in the Tail-Flick Assay in Mice

| Compound | Dose Range (μg/kg, s.c.) | ED$_{50}$ at 5 min (μg/kg) |
|---|---|---|

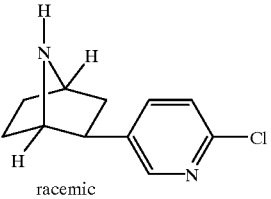

racemic

CMI-477

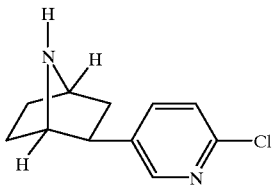

CMI-488

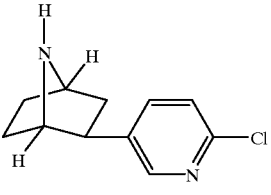

CMI-489

TABLE II

Antagonism of epibatidine antinociception in mice

| | Dose | % MPE | | |
|---|---|---|---|---|
| Drugs | (mg/kg) | mean | SE | P value* |
| 0.9% NaCl | | 95 | 3 | |
| mecamylamine | 1 | 4 | 2 | <0.001 |
| hexamethonium | 3 | 50 | 18 | <0.05 |
| naloxone | 3 | 82 | 13 | <0.05 |
| yohimbine | 3 | 69 | 17 | <0.05 |
| atropine | 3 | 94 | 6 | <0.05 |

*As compared with vehicle (0.9% Nacl) effect.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of agonizing the human central nervous system nicotine receptor $N_n$, the method comprising administering to a patient in need of central nervous system nicotine receptor $N_n$ agonizing an effective nicotine agonist amount of a compound selected from the group consisting of CMI-488, of the structure

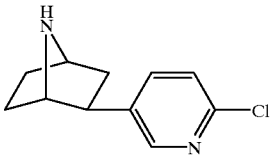

in the d stereoconfiguration,
CMI-489, of the structure

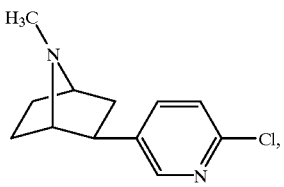

CMI-477, of the structure

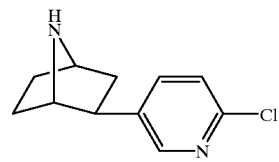

in the l stereoconfiguration,
CMI-526, of the structure

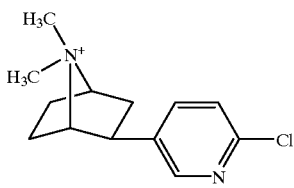

CMI-495, of the structure

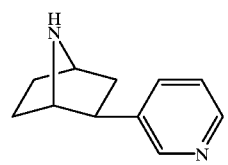

or pharmaceutically acceptable salt thereof, in a physiologically acceptable carrier, wherein the effective amount ranges from about 0.1 to about 20 μg/kg body weight of the patient.

* * * * *